United States Patent [19]
Gomibuchi

[11] Patent Number: 5,305,391
[45] Date of Patent: Apr. 19, 1994

[54] METHOD OF AND APPARATUS FOR INSPECTING BOTTLE OR THE LIKE

[75] Inventor: Tadashi Gomibuchi, Tokyo, Japan

[73] Assignee: Toyo Glass Company Limited, Tokyo, Japan

[21] Appl. No.: 761,524

[22] Filed: Sep. 18, 1991

[30] Foreign Application Priority Data

Oct. 31, 1990 [JP] Japan ................................. 2-291776

[51] Int. Cl.⁵ .......................... G01N 21/88; G06K 9/00
[52] U.S. Cl. ...................................... 382/8; 250/223 B; 356/240; 382/50; 348/127
[58] Field of Search .................. 382/8, 50; 250/223 B; 356/240; 209/526; 358/101, 106

[56] References Cited

U.S. PATENT DOCUMENTS

| | | | |
|---|---|---|---|
| 4,488,648 | 12/1984 | Claypool | 250/223 B |
| 4,606,635 | 8/1986 | Miyazawa et al. | 356/240 |
| 4,679,075 | 7/1987 | Williams et al. | 209/526 |
| 4,691,231 | 9/1987 | Fitzmorris et al. | 250/223 B |
| 4,807,995 | 2/1989 | Dassler et al. | 209/526 |
| 4,924,083 | 5/1990 | Ishikawa et al. | 356/240 |
| 4,931,632 | 6/1990 | Brandt | 250/223 B |
| 4,972,493 | 11/1990 | Chenaly | 382/8 |
| 5,007,096 | 4/1991 | Yoshida | 382/8 |

Primary Examiner—Leo H. Boudreau
Assistant Examiner—Larry J. Prikockis
Attorney, Agent, or Firm—Sughrue, Mion, Zinn, Macpeak & Seas

[57] ABSTRACT

A method of and an apparatus for inspecting a bottle or the like by which the presence or absence of a defect, particularly a check, can be determined with a high degree of accuracy. Light is irradiated upon an inspection area of a rotating or moving object, and reflected light is photographed by a two-dimensional camera which includes solid-state image pickup elements. Picture element data for a first frame are fetched at a first point of time from the two-dimensional camera and stored into a memory, and then picture element data for a second frame are fetched at a second point of time after a fixed interval of time after the first point of time. Then, differences of the picture element data for the second frame from the picture element data for the first frame from the memory are taken and binary digitized with reference to predetermined brightness threshold level, and the differences which have one of two binary values are counted. The count number is compared with a predetermined number to determine the presence or absence of a defect in the object being inspected.

6 Claims, 6 Drawing Sheets

METHOD OF AND APPARATUS FOR INSPECTING BOTTLE OR THE LIKE

BACKGROUND OF THE INVENTION

1. Field of the Invention

This invention relates to a method of and an apparatus for inspecting a bottle or the like using an optical device to determine presence or absence of a defect by electronic processing.

2. Description of the Prior Art

Various methods of optically inspecting a bottle or the like to determine the presence or absence of a defect such as, for example, a split often referred to as a check or a foreign article such as a stone or the like) which may appear at or mixed in a bottom or body portion of the bottle are conventionally known. An exemplary one of such methods is disclosed, for example, in Japanese Patent Publication Application No. 58-58020. According to the method, light is irradiated in an inverted conical ring shape by a light projecting section upon circumferential side wall of a bottle for inspection from above such that it may be introduced toward a bottom face of the bottle so as to reach a corner material portion of the bottom through the material of the side wall of the bottle. The light which is reflected from a split in the corner material portion is introduced into a single photoelectric transducer element to detect such a split.

The method, however requires an optical system which is complicated in construction. In addition, since reflected light is detected only by means of the single photoelectric transducer element, if the angle of light reflected from a check is different only a little from a specified angular range, such reflected light will not be introduced into the photoelectric transducer element, and consequently, the presence or absence of a defect cannot be detected accurately. Further, various design patterns are commonly formed on bottom faces of bottles, and the amount of reflected light is varied to a great extent depending upon such design pattern. Accordingly, it is impossible to detect a check of a bottle only from a variation in amount of light when the bottle has a design pattern thereon.

Another exemplary one of such conventional methods as described above is disclosed in Japanese Patent Laid-Open Application No. 61-107144. According to the method, a bottle is carried in to an inspection position in the neighborhood of a one-dimensional image sensor, and while the bottle is being rotated around an axis thereof with the axis thereof held in parallel to a longitudinal direction of the image sensor, it is illuminated such that an image of transmission light through the bottle is formed on the image sensor. The image sensor is scanned so as to obtain a set of signals, and such scanning &s repeated during rotation of the bottle so as to successively obtain a plurality of sets of signals. Two sets of signals obtained at a first rotational position of the bottle and a second rotational position of the bottle after rotation of the bottle from the first rotational position are compared with each other, and presence or absence of a defect is determined in accordance with a result of such comparison.

With the method, the accuracy in detection is somewhat higher than that of the former method described above. However, while employment of a one-dimensional image sensor is more advantageous in regard to resolution than employment of a two-dimensional image sensor, a high degree of accuracy cannot be anticipated for detection of a check of a bottle using a one-dimensional image sensor since the direction of reflected light from a check of a bottle is changed to a great extent by rotation of the bottle and since such checks are various in shape and further since more disturbance light from other than a check is received by the one-dimensional Image sensor due to rotation of the bottle. Accordingly, the latter method cannot cope efficiently with cheeks of bottles having various shapes.

SUMMARY OF THE INVENTION

It is an object of the present invention to provide a method of and an apparatus for inspecting a bottle or the like by which presence or absence of a defect, particularly of a check, can be determined with a high degree of accuracy.

In order to attain the object, according to an aspect of the present invention, there is provided a method of inspecting an object for inspection such as a bottle or the like being rotated or moved at a predetermined speed to detect a defect of the object, which comprises the steps of irradiating light upon an inspection area of the object being rotated or moved, photographing reflected light from the inspection area of the object by means of a two-dimensional camera which includes solid-state image pickup elements, fetching picture element data for a first frame at a first point of time from the two-dimensional camera and storing the data into a memory, fetching picture element data for a second frame at a second point of time after a fixed interval of time after the first point of time, calculating differences of the picture element data for the second frame from the picture element data for the first frame from the memory, binary digitizing the differences with reference to a predetermined brightness threshold level, counting a number of the differences which have one of two binary values, and comparing the count number with a predetermined number to determine presence or absence of a defect in the object for inspection.

In case the object for inspection is, for example, a bottle and has a check as a defect, since the direction of reflected light from the check is instantaneously changed to a great extent by rotation or movement of the bottle, even if picture element data originating from such reflected light are fetched at a certain point $T_1$ of time from the two-dimensional camera as a picture element at a certain position, picture element data originating from reflected light of the check are not fetched at another point $T_2$ of time after the predetermined interval of time. On the other hand, since disturbance light from any location other than the check is reflected almost in the same direction also after some rotation or movement of the object, picture element data are fetched at both of the points $T_1$ and $T_2$ of time.

Accordingly, if differences are taken between picture element data for one frame fetched from the two-dimensional camera at the point $T_1$ of time and picture element data for another frame fetched at the point $T_2$ of time after the predetermined interval of time after the point $T_1$ of time, then picture element data of high brightness values originating from reflected light from the check remain, but picture element data originating from disturbance light from any other portion than the cheek are cancelled. Thus, such differences are subsequently binary digitized or divided into two groups of white and black with reference to a predetermined brightness threshold level, and a number of those picture elements having differences which have one of two binary values is counted. Then, when the count number is greater than the predetermined number, it is determined that there is a defect in the object. Consequently, presence or absence of a check which makes a defect can be detected with a high degree of accuracy.

If the speed of rotation or movement of the object changes, then also the direction of reflected light from such check is changed and the amount of incidence light to the two-dimensional camera is changed. Accordingly, preferably the fixed interval of time between frames at which picture element data are to be fetched and the brightness threshold level for binary digitization are adjusted in response to a speed of the object for inspection in order to improve the accuracy in detection. Consequently, when data for each one frame from the two-dimensional camera are to be fetched at a high speed, the number of frames to be thinned out is adjusted in response to the speed of rotation or movement of the object.

Preferably, a number of those of the differences which have one of two binary values is counted for each of a plurality of window areas included in a photographing area of the two-dimensional camera in order to except such picture elements originating from a design pattern formed on the object for inspection. The two-dimensional camera can thus detect presence or absence of a defect of the object for inspection with a high degree of accuracy for the plurality of locations of the object without detecting a design pattern or the like as a defect in error.

According to another aspect of the present invention, there is provided an apparatus for inspecting an object for inspection such as a bottle or the like being rotated or moved at a predetermined speed by a handling machine to detect a defect of the object, which comprises a light projector for irradiating light upon an inspection area of an object for inspection being rotated or moved, a two-dimensional CCD (charge-coupled device) camera for photographing reflected light from the object only for a fixed area, a camera controller for successively fetching picture element data produced from the two-dimensional CCD camera for each one frame after each predetermined interval of time and storing the thus fetched picture element data therein, a difference calculating section for calculating differences between the picture element data thus fetched for different frames, a binary digitizing section for binary digitizing the thus calculated differences with reference to a predetermined brightness threshold level, a counter for counting a number of those of the differences which have one of two binary values, and a main controller for adjusting the predetermined interval of time for the camera controller and the predetermined bright threshold level for the binary digitizing section in response to a speed signal from the handling machine representative of a speed of the object and for counting a number of those of the differences which have one of two binary values and comparing the count number with a predetermined number to determine presence or absence of a defect in the object for inspection.

With the apparatus, presence or absence of a defect in an object for inspection can be detected with a high degree of accuracy with a minimized influence of disturbance light.

The apparatus may further comprise means for causing the counter to count a number of those of the differences which have one of two binary values only for one or ones of a plurality of window areas included in a photographing area of the two-dimensional CCD camera which is or are designated by the main controller.

Preferably, the apparatus further comprises a monitoring display apparatus for reproducing and displaying thereon data for a frame fetched by the camera controller so that setting for inspection can be performed appropriately and readily while a condition of a defect is being observed.

The above and other objects, features and advantages of the present invention will become apparent from the following description and the appended claims, taken in conjunction with the accompanying drawings.

DESCRIPTION OF THE PREFERRED EMBODIMENT

Figure 2:
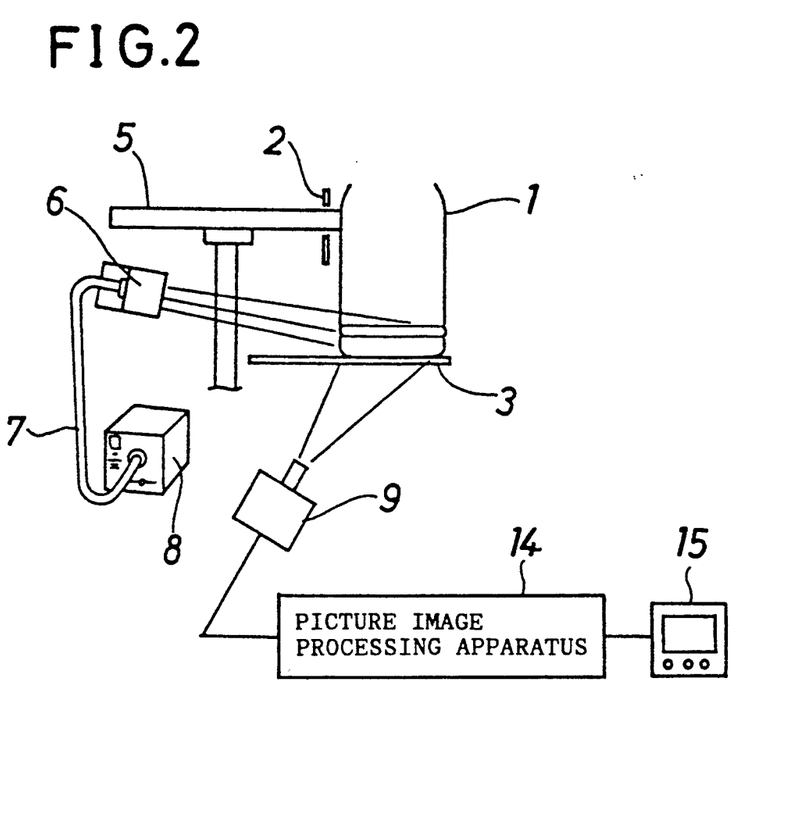
FIG. 2 is a diagrammatic representation illustrating a defect detecting method according to the present invention.
Figure 3:
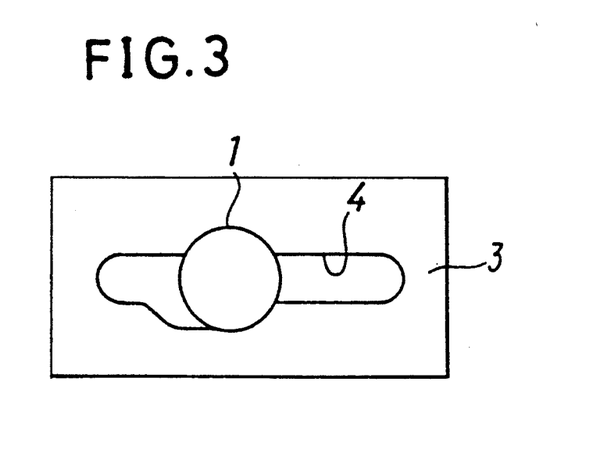
FIG. 3 is a plan view showing a relationship between a bottle and an inspection window in a detecting operation in the method illustrated in FIG. 2.

Referring first to FIG. 2, there is illustrated a defect detecting method to which the present invention is applied. A transparent or translucent bottle 1 which is an object for inspection is transported along a guide rail 2 to an inspection window 4 (FIG. 3) formed in a table 3. At the position of the inspection window 4, light is irradiated from a light projector 6 upon the bottle 1 while the bottle 1 is being rotated at a fixed speed by a drive disk 5. The light projector 6 is connected to a halogen light source 8 by way of an optical fiber 7 and projects light from the halogen light source 8 in a slight oblique downward direction toward a bottom portion of the bottle 1. Below the inspection window 4, a two-dimensional CCD camera 9 is installed such that an optical axis thereof makes a predetermined angle with respect to an optical axis of the light projector 6. The two-dimensional CCD camera 9 photographs, through the inspection window 4 of the table 3, a portion of the bottom of the bottle 1 illuminated with light from the light projector 6.

Figure 4:
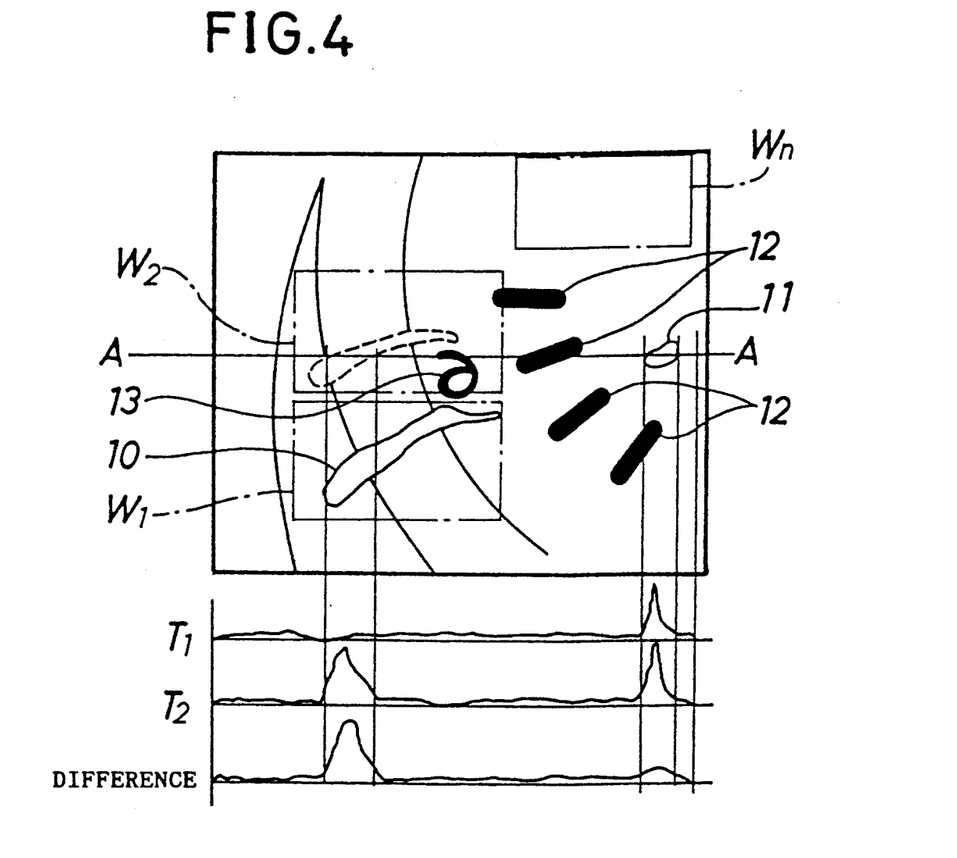
FIG. 4 is a diagrammatic view illustrating a picture image for one frame of a two-dimensional CCD camera and analog waveforms in brightness level obtained along a certain line of the picture image.

Referring now to FIG. 4, there is shown, In a rectangular screen, a picture image for one frame photographed by the two-dimensional CCD camera 9 at a point $T_1$ of time. In the arrangement shown in FIG. 2, the two-dimensional CCD camera 9 photographs only part of the bottom of the bottle 1, and a white picture image 10 originates from the light reflected from a check formed in a circumferential edge portion of the bottom of the bottle 1 which is high in brightness. Another small white picture image 11 originates from disturbance light from some portion other than the cheek (for example, reflected light from a portion of the table 3). A plurality of regularly spaced black picture images 12 originate from projected portions which may be provided on the bottom of the bottle 1 in order to indicate a model number and so forth of the bottle 1 in a code system. Another black picture image 13 originates from a design pattern provided on the bottom face of the bottle 1. Since the direction of reflected light from the check is instantaneously changed to a great extent if the bottle 1 is rotated only a little as described hereinabove, the picture image 10 originating from the cheek moves, at another point $T_2$ of time after a short predetermined interval of time after the point $T_1$ of time, to a great extent as indicated by a broken line in the photographing screen of the two-dimensional CCD camera 9 while the picture image 11 originating from disturbance light from portions other than the check moves much less.

Referring back to FIG. 2, a picture image processing unit 14 is connected to the two-dimensional CCD camera 9. Picture element data produced from the camera 9 are accepted by the picture element processing unit 14 for each frame and stored into a memory (not shown) of the picture element processing unit 14. The picture element data thus stored in the memory are thereafter processed as hereinafter described. A monitoring television set 15 in the form of a cathode ray tube is connected to the picture image processing unit 14 so that a picture image accepted into the picture image processing unit 14 can be displayed at any time on the television set 15.

Figure 1:
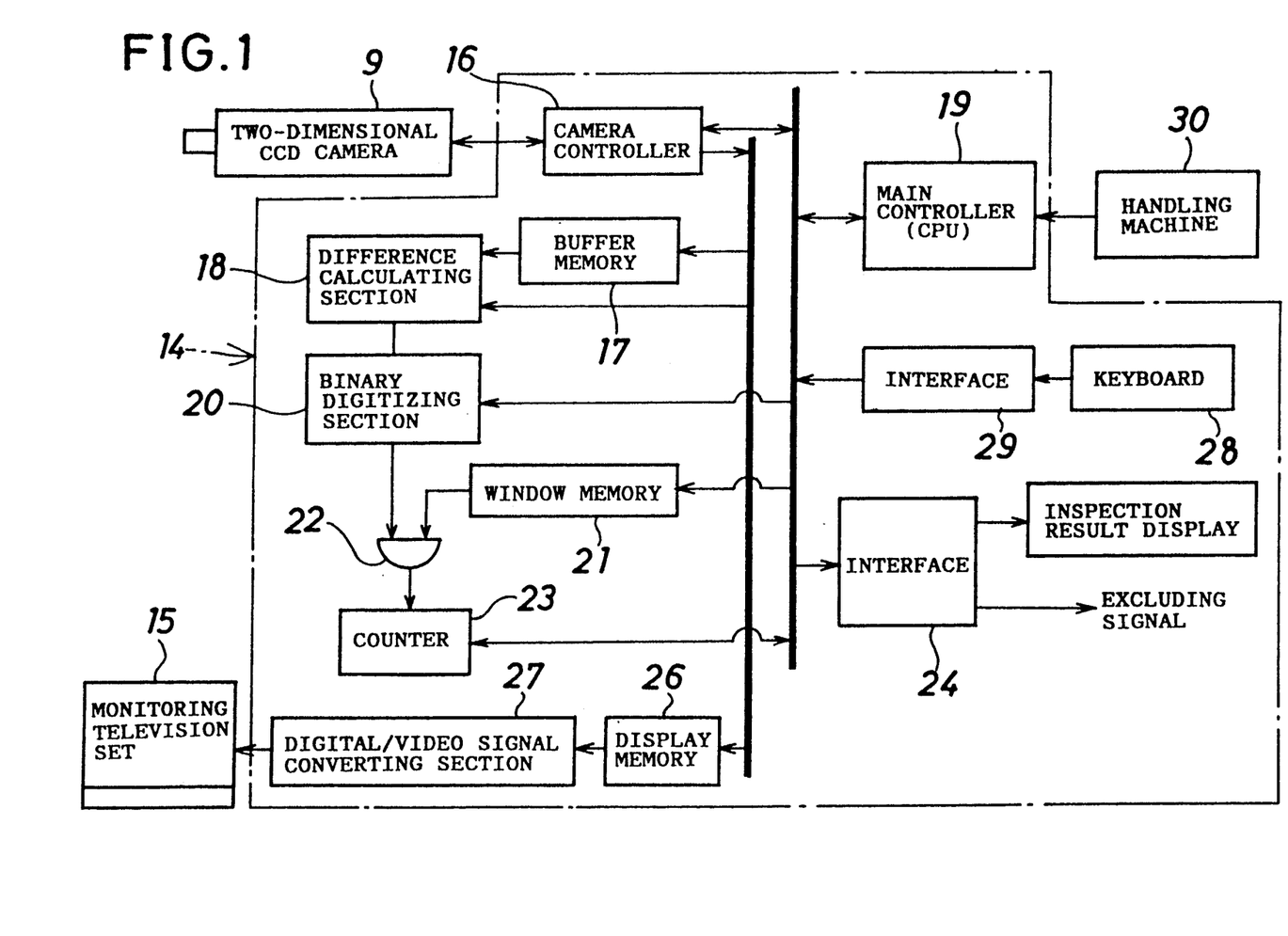
FIG. 1 is a block diagram of a defect detecting apparatus to which the present invention is applied.

The picture image processing unit 14 has a general construction as shown in FIG. 1. Referring to FIG. 1, a large number of picture element data for one frame obtained from the two-dimensional CCD camera 9 are inputted to a camera controller 16 for each one frame. Thus, picture element data are successively inputted to the camera controller 16, for example, for a total of 115 frames for one full rotation of the bottle 1 at a time interval of a fixed short time t and stored into a memory not shown therein. Picture element data for one frame designated by a main controller 19 are outputted from the camera controller 16 and stored once into a buffer memory 17, and differences of different picture element data for a next designated one frame which are inputted after an interval of time of $t \times k$ after the certain point of time are calculated at a difference calculating section 18. It is to be noted that k is a thinning out value and is set in such a manner as hereinafter described by the main controller 19 which has a CPU (central processing unit) not shown therein. Here, the reason why differences between picture image data for two frames obtained at different times different by $t \times k$ are calculated is that it is intended to extract only such picture image 10 as shown in FIG. 4 which originates from a check of a bottle.

In particular, referring to FIG. 4, a picture element output of the two-dimensional CCD camera 9 is taken in the form of an analog waveform along a straight line A—A of the rectangular photographing screen at different rotational positions of the bottle 1 and is shown in waveform diagram in a corresponding relationship with the picture image below the photographing screen. Thus, at the point $T_1$ of time at which the picture image 10 originating from the check is at a full line position, the waveform presents a high level or peak only at a portion thereof which corresponds to the picture image 11 originating from disturbance light. On the other hand, at the point $T_2$ of time after the interval of time $t \times k$, the picture image 11 originating from disturbance light move very little, but the picture image 10 originating from the check has moved much more and is now at the broken line position. Consequently, the analog waveform exhibits high levels or peaks at a portion thereof which corresponds to the picture image 11 originating from disturbance light and another portion which corresponds to the picture image 10 originating from the check. Thus, if a difference between the brightness values at the point $T_1$ of time and the point $T_2$ of time is taken, then the peak at the portion corresponding to the picture image 10 originating from the check remains, but the other peak at the portion corresponding to the picture image 11 originating from disturbance light is cancelled.

The reason why differences are taken between picture image data for two frames obtained at times different by the interval of time $t \times k$ is that, when the bottle 1 is rotated at a very high speed, the calculation of differences between successive frames for the total of 115 frames for one full rotation of the bottle 1 may not be performed. In order to avoid such a possible circumstance, frames different more than one frame distance are selected for calculating the differences. The value of the thinning out value k is thus determined in response to a speed of rotation of the bottle 1 such that, while the speed of rotation of the bottle 1 rises, the interval of time $t \times k$ may not be varied significantly.

Referring back to FIG. 1, the differences in picture element data calculated at the difference calculating section 18 are then binary digitized for each picture element by a binary digitizing section 20 with reference to a certain level of brightness or threshold level. In other words, a certain brightness level is determined as a reference or threshold level, and picture element data are divided into two groups of white and black such that, if the picture element data are equal to or higher than the certain brightness threshold level, then they are determined as white (1 in binary digital value), but if they are lower than the predetermined brightness threshold level, then they are determined as black (0 in binary digital value). Such binary digitization is performed successively for all of picture elements for one frame. Further, the level H serving as the reference level for binary digitization is automatically adjusted in response to a speed of rotation of the bottle 1 by the main controller 19. The reason is that, when the speed of rotation of the bottle 1 is high, the amount of incidence light to the two-dimensional CCD camera for photographing one frame and hence output levels of individual solid-state image pickup elements are low correspondingly.

Since the picture image 10 originating from the check can be regarded as an aggregate of picture elements having higher brightness values than the reference brightness level for binary digitization and will likely appear at any particular location of the rectangular photographing screen of FIG. 4 (due to the fact that a check can appear at any particular location of the bottom or body of a bottle) the rectangular photographing screen of FIG. 4 is divided into first to n-th window areas $W_1$, $W_2$, ... and $W_n$, where the picture image 10 of a check is apt to appear. A number of those of picture elements which are determined as white by binary digitization (defect picture elements) is counted individually for each of the window areas $W_1$, $W_2$, ... and $W_n$. Thus, it can be presumed that, if the number of such defect picture elements in a window area is greater than a predetermined value, then a check is present in the window area.

Thus, data representative positions of individual picture elements in a window area are stored into a window memory 21 in accordance with an instruction from the main controller 19, and only the binary data representing white from the binary digitizing section 20 which belong to the window area will pass through a gate circuit 22 and be counted by a counter 23. Consequently, the count value of the counter 23 represents a number of defect picture elements in the window area, and in case the count value is higher than a fixed level, the main controller 19 determines that there is a cheek in the bottle 1 and outputs, by way of an interface 24, an excluding signal to the handling machine 30 to exclude the defective bottle 1 from the transporting line. The main controller 19 further controls an inspection result display unit 25 to display a number of such defective bottles, a defective location and so forth.

Picture element data for each one frame fetched into the camera controller 16 are stored in digital amount into a display memory 26 in a predetermined period set by the main controller 19 and are then converted into a video signal by a digital/video signal converting section 27 so that they are reproduced by and displayed on the monitoring television set 15. Initial set values and so forth necessary for inspection are previously inputted to the main controller 19 by way of an interface 29 from a keyboard 28 while a reproduced image on the television set 15 is being observed by an operator.

An inspection timing signal, a bottle presence signal representing that a bottle is present at a predetermined inspection position, a speed signal representing a speed of rotation of such bottle and so forth are inputted from a handling machine 30 to the main controller 19. The thinning out value k and the reference level H for binary digitization described above are adjusted in accordance with the thus inputted speed signal. As already known, the handling machine 30 performs various operations including transporting a bottle 1 and rotating the bottle 1 at the inspection position by means of the drive disk 5 as described above. Alternatively, a speed of rotation of the bottle 1 may be measured by counting a number of inspection timing signals received by the main controller 19 for a unit period of time.

Figure 5A:
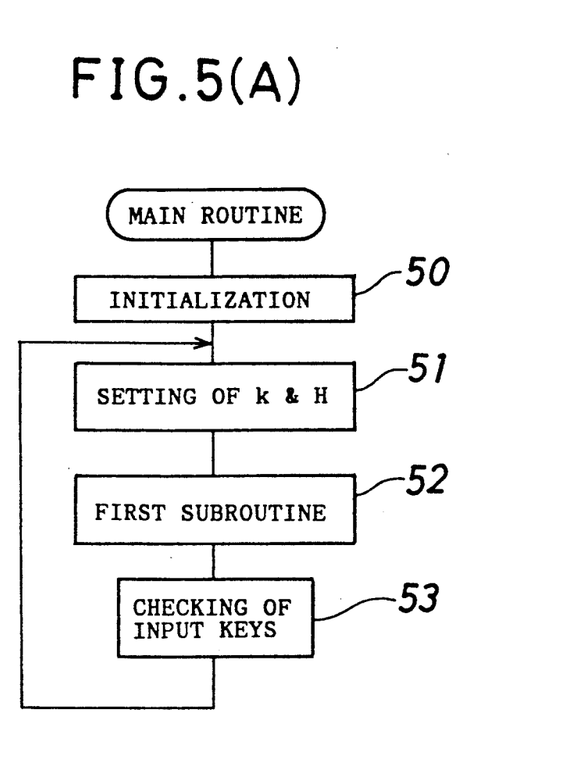
FIGS. 5(A), 5(B) and 5(C) are flow charts illustrating operation of the defect detecting apparatus of FIG. 1.
Figure 5B:
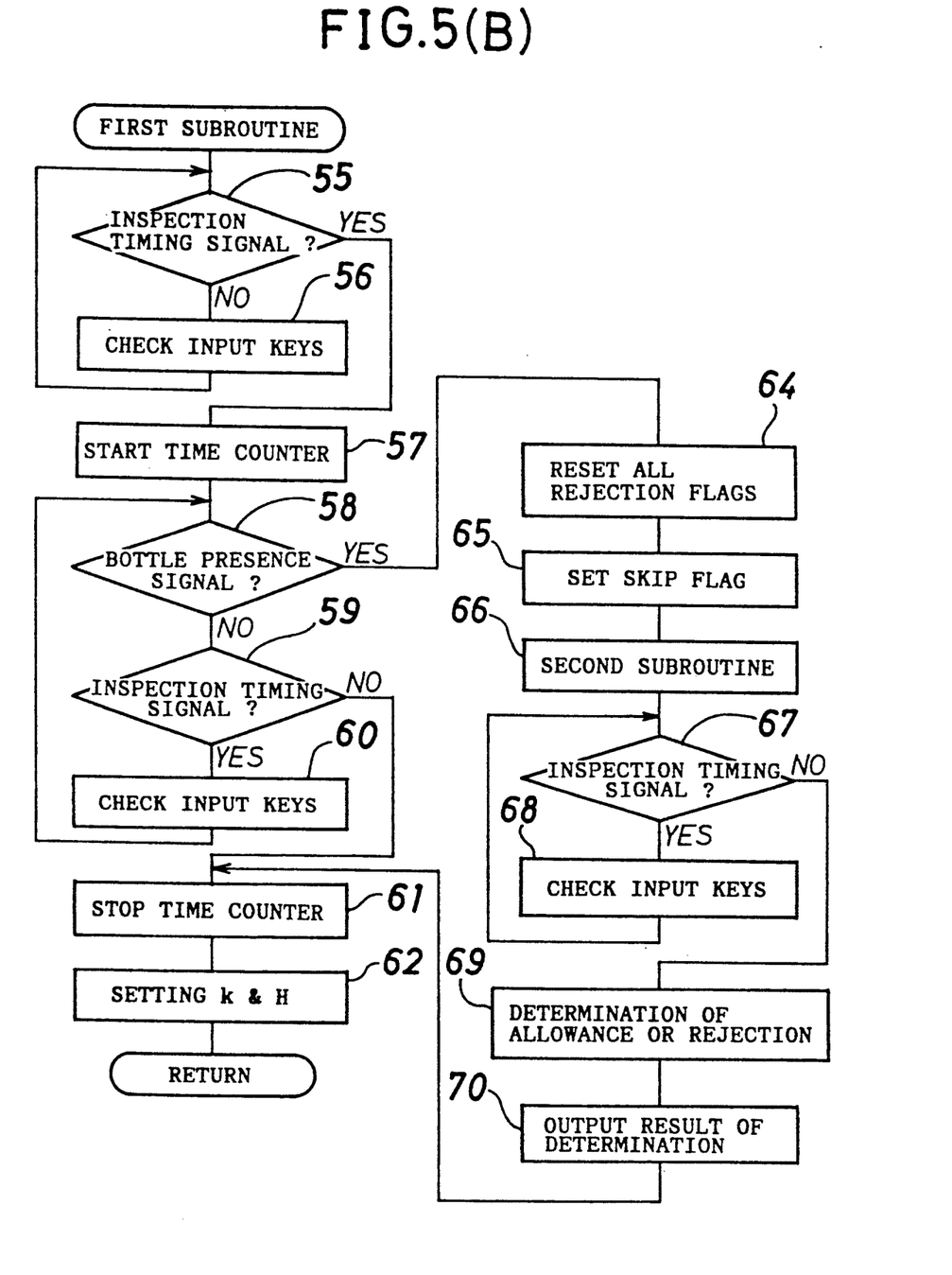
Figure 5C:
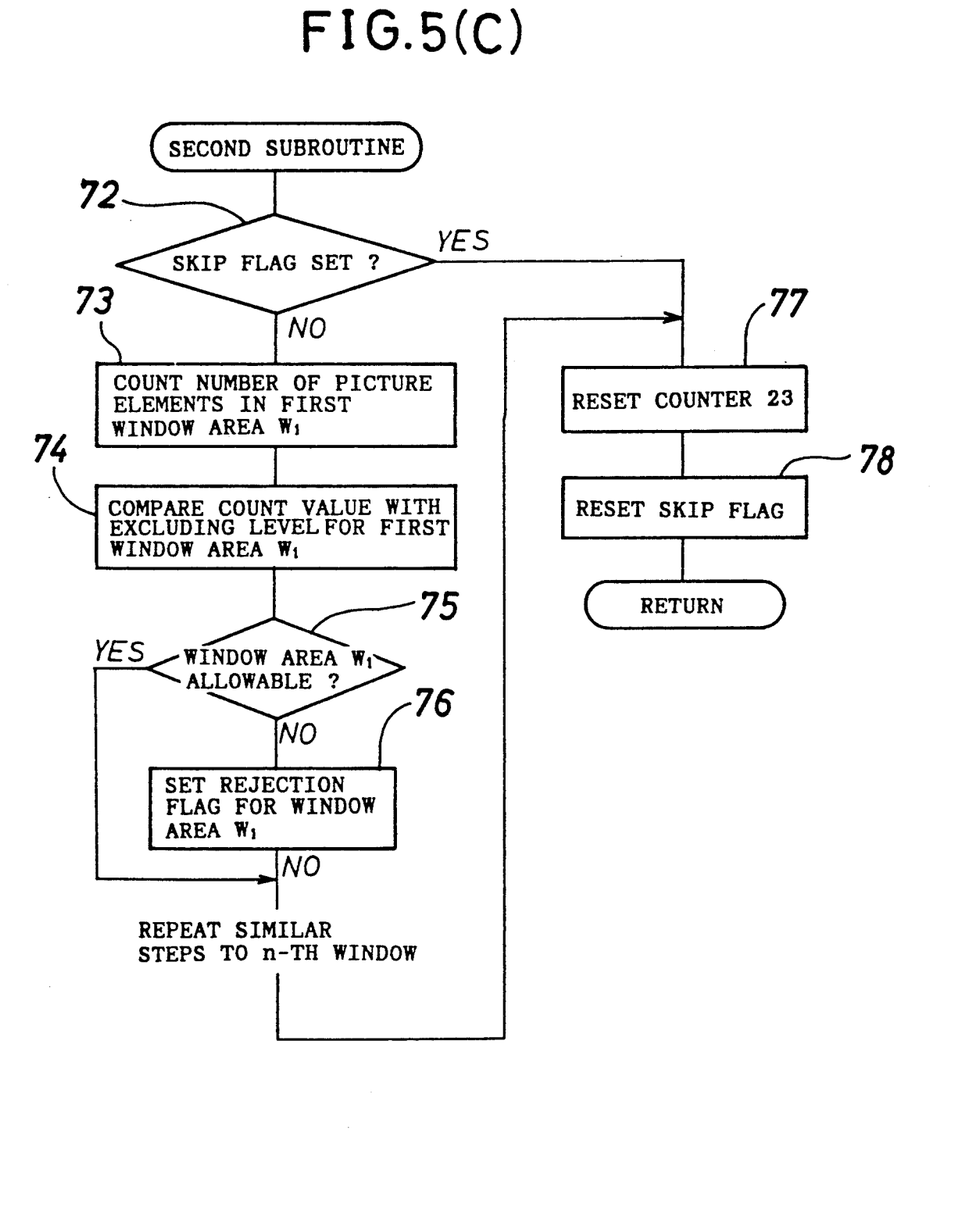

Operation of the main controller 19 is illustrated in FIGS. 5(A) to 5(C). Referring first to FIG. 5(A) in which a main routine is shown, various initializing operations are executed at step 50, and then at step 51, the thinning out value k and reference level H for binary digitization as described above are set in accordance with a speed signal from the handling machine 30 or a speed measured from inspection timing signals. Then at step 52, a first subroutine as shown in FIG. 5(B) is executed, and then at step 53, input keys of the keyboard 28 are checked, whereafter the control sequence returns to step 51.

When the first subroutine is entered, it is judged at step 55 whether or not there is an inspection timing signal, and if there is no inspection timing signal, then conditions of the input keys of the keyboard 28 are checked at step 56, whereafter the control sequence returns to step 55 to repeat a similar sequence of operations. On the contrary if there is an inspection timing signal at step 55, then the control sequence advances to step 57, at which counting of a counter for measuring an inspection time is started, and then in step 58, it is judged whether or not there is a bottle presence signal, that is, whether a bottle 1 is present at the inspection position. Then, if a bottle 1 is present, all rejection flags are reset at step 64, and a skip flag is set at step 65. The skip flag is provided so that picture element data for a first frame received by the camera controller 16 may be stored into the buffer memory 17. Thus, the skip flag is set in the first control cycle. Subsequently, a second subroutine shown in FIG. 5(C) is executed.

Referring now to FIG. 5(C), after the second subroutine is entered, it is judged first at step 72 whether the skip flag is in a set state. Since the skip flag is in a set state in the first control cycle, the control sequence advances to step 77, at which the counter 23 of FIG. 1 is reset, and then to step 78, at which the skip flag is reset, whereafter the control sequence returns to the first subroutine of FIG. 5(B).

Since the skip flag is in a reset state at step 72 in the second or succeeding control cycle, the control sequence advances to step 73, at which a number of defect picture elements in the first window area $W_1$ is counted by the counter 23 as described hereinabove, and then in step 74, the count value is compared with a fixed excluding level set for the first window area $W_1$. Then, a judgment for allowance or rejection for the window area $W_1$ is made at step 75 in accordance with a result of such comparison. If the Judgment is a rejection, a rejection flag is set for the window area $W_1$ at step 76, but in the case of an allowance, the control sequence advances to a step for the second window area $W_2$ skipping the step 76. Then, similar operations to those at steps 73 to 76 are repeated to the last n-th window area $W_n$, and after completion of such judgment, the control sequence returns to the first subroutine of FIG. 5(B) by way of steps 77 and 78.

After the control sequence returns to the first subroutine of FIG. 5(B), the presence or absence of an inspection timing signal is determined at step 67, and if there is an inspection timing signal, then conditions of the input keys are checked at step 68, whereafter the control sequence returns to step 67. If there is no inspection timing signal at step 67, then the main controller 19 checks all of the rejection flags for the windows $W_1$ to $W_n$ and determines, when all of the rejection flags are not in a set state, that the bottle 1 is allowable, but determines, when at least one of the rejection flags is in a set state, that a check is present at a corresponding window and accordingly the bottle 1 is to be rejected. Then, a result of the determination is outputted to the handling machine 30 at step 70. In particular, when the determination at step 69 is a rejection, the main controller 19 outputs, by way of the interface 24, an excluding signal to the handling machine 30 to exclude the defective bottle 1 from the transporting line. The inspection time measuring counter is then stopped at step 61, and then the thinning out number k and the reference level H for binary digitization are newly set at step 62, whereafter the control sequence returns to the main routine of FIG. 5(A).

In case there is no bottle presence signal at step 58, the presence or absence of an inspection timing signal is determined at step 59, and if there is an inspection timing signal, then conditions of the input keys of the keyboard 28 are checked at step 60, whereafter the control sequence returns to step 58. On the contrary, if there is no inspection timing signal, the inspection time measuring counter is stopped at step 61 as described hereinabove, whereafter the control sequence returns to the main routine of FIG. 5(A) by way of the step 62.

It is to be noted that, while the presence or absence of a check at a bottom portion of a bottle 1 is being detected while the bottle 1 is being rotated in the embodiment described above, the presence or absence of a check at any portion other than the bottom portion can be inspected so well. Further, it is also possible to inspect a bottle 1 while the bottle 1 is being moved, for example, along a horizontal path. Further, the presence or absence not only of a check but also of a white foreign article can be detected. Furthermore, the object for inspection is not limited to a bottle, and the present invention can be applied also to inspection of a glass, transparent or translucent plastic vessel and so forth.

Having now fully described the invention, it will be apparent to one of ordinary skill in the art that many changes and modifications can be made thereto without departing from the spirit and scope of the invention as set forth herein.

What is claimed is:

1. A method of inspecting a rotating or moving object for detecting a defect in the object, comprising the steps of irradiating light upon an inspection area of the object from an angle between a line extending perpendicular to a rotational axis of the object and the rotational axis of the object, photographing reflected light from the inspection area of the object by a two-dimensional camera, storing picture element data corresponding to a first frame at a first point of time of the photographed reflected light into a memory, storing picture element data corresponding to a second frame at a second point of time of the photographed reflected light after a fixed interval of time after the first point of time, said fixed interval of time being determined based on a predetermined period of time and a thinning out value that is determined based on a rotating speed of the object, calculating differences of the picture element data between the first and second frames, binary digitizing the differences with reference to a predetermined brightness threshold level, counting a number of the differences which have one of two binary values, and comparing the count number with a predetermined number to determine the presence or absence of a defect in the object.

2. A method as claimed in claim 1, wherein the brightness threshold level for binary digitization is adjusted in response to a speed of the object.

3. A method as claimed in claim 1, wherein a number of the differences which have one of two binary values is counted for each of a plurality of window areas included in a photographing area of said two-dimensional camera.

4. An apparatus for inspecting a rotating or moving object for detecting a defect in the object, comprising a light projector for irradiating light upon an inspection area of the object from an angle between a line extending perpendicular to a rotational axis of the object and the rotational axis of the object, a two-dimensional CCD camera for photographing reflected light from a fixed area of the object, a camera controller for successively fetching picture element data produced from said two-dimensional CCD camera for successive frames separated in time by a predetermined interval of time, said predetermined interval of time being determined based on a predetermined period of time and a thinning out value that is determine based on a rotating speed of the object, a memory for storing the fetched picture element data, a difference calculating circuit for calculating differences between the picture element data for different frames, a binary digitizing circuit for binary digitizing the calculated differences in accordance with a predetermined brightness threshold level, a counter for counting a number of the differences which have one of two binary values, and a main controller including means for adjusting the thinning out value and the predetermined brightness threshold level for said binary digitizing circuit in response to a speed signal representative of a speed of the rotating or moving object and means for counting a number of the differences which have one of two binary values, and means for comparing the count number with a predetermined number to determine the presence or absence of a defect in the object.

5. An apparatus as claimed in claim 4, wherein said main controller further comprises means for causing said counter to count a number of the differences which have one of two binary values for at least one of a plurality of window areas included in a photographing area of said two-dimensional CCD camera.

6. An apparatus as claimed in claim 4, further comprising a monitoring display apparatus for reproducing and displaying thereon data for a frame fetched by said camera controller.

* * * * *